US012150952B2

(12) United States Patent
Hofmann et al.

(10) Patent No.: US 12,150,952 B2
(45) Date of Patent: Nov. 26, 2024

(54) FORMULATION FOR THE USE IN THE SIMULTANEOUS TREATMENT OF COCCIDIAL INFECTIONS AND IRON DEFICIENCIES

(71) Applicant: Elanco Animal Health GmbH, Monheim am Rhein (DE)

(72) Inventors: Stefan Hofmann, Langenfeld (DE); Kirsten Borngen, Feldhasenweg (DE); Maya Vinzing, Hosfelds Katernberg (DE)

(73) Assignee: Elanco Animal Health GmbH, Monheim Am Rhein (DE)

( * ) Notice: Subject to any disclaimer, the term of this patent is extended or adjusted under 35 U.S.C. 154(b) by 765 days.

(21) Appl. No.: 15/734,847

(22) PCT Filed: May 29, 2019

(86) PCT No.: PCT/EP2019/064055
§ 371 (c)(1),
(2) Date: Dec. 3, 2020

(87) PCT Pub. No.: WO2019/233870
PCT Pub. Date: Dec. 12, 2019

(65) Prior Publication Data
US 2021/0228612 A1 Jul. 29, 2021

(30) Foreign Application Priority Data
Jun. 5, 2018 (EP) .................... 18176138

(51) Int. Cl.
| *A61K 31/715* | (2006.01) |
| *A61K 9/00* | (2006.01) |
| *A61K 31/53* | (2006.01) |
| *A61K 47/10* | (2017.01) |
| *A61K 47/12* | (2006.01) |
| *A61K 47/26* | (2006.01) |
| *A61K 47/32* | (2006.01) |
| *A61K 47/44* | (2017.01) |

(52) U.S. Cl.
CPC .......... *A61K 31/715* (2013.01); *A61K 9/0019* (2013.01); *A61K 9/0053* (2013.01); *A61K 31/53* (2013.01); *A61K 47/10* (2013.01); *A61K 47/12* (2013.01); *A61K 47/26* (2013.01); *A61K 47/32* (2013.01); *A61K 47/44* (2013.01)

(58) Field of Classification Search
None
See application file for complete search history.

(56) References Cited

U.S. PATENT DOCUMENTS

| 2003/0181451 A1 | 9/2003 | Greif et al. |
| 2006/0240049 A1 | 10/2006 | De Spiegeleer et al. |
| 2014/0127320 A1 | 5/2014 | Salamone et al. |
| 2015/0313940 A1* | 11/2015 | Le Meur ................ A61K 45/06 206/219 |
| 2021/0228613 A1 | 7/2021 | Hofmann et al. |

FOREIGN PATENT DOCUMENTS

| CL | 2020003132 A1 | 6/2021 |
| CN | 102973502 A | 3/2013 |
| CN | 105007944 A | 10/2015 |
| CN | 108066767 | 5/2018 |
| DE | 2413722 | 10/1975 |
| DE | 2718799 | 11/1978 |
| EP | 2740469 | 6/2014 |
| JP | 2016505558 A | 2/2016 |
| WO | 1999/62519 | 12/1999 |
| WO | 2002/13831 A1 | 2/2002 |
| WO | 2002/14288 | 2/2002 |
| WO | 2008145281 | 12/2008 |
| WO | 2014086958 | 6/2014 |
| WO | 2014086959 | 6/2014 |
| WO | 2014086960 | 6/2014 |
| WO | 2016/131853 | 8/2016 |
| WO | 2016131583 A1 | 8/2016 |
| WO | 2019/233867 A1 | 12/2019 |

OTHER PUBLICATIONS

Wong, Mol Pharm. Feb. 3, 2014; 11(2): 531-544. (Year: 2014).*
Mohajeri, E-Journal of Chemistry 2012, 9(4), 2268-2274. (Year: 2012).*
Li, CN 102973502 A, Mar. 20, 2013, machine translation. (Year: 2013).*
Griffin WC, "Calculation of HLB values of non-ionic surfactants", Journal of the Society of Cosmetic Chemists, (19540000), pp. 249-256, XP000671451.
Davies JT, "A quantitative kinetic theory of emulsion type, I. Physical chemistry of the emulsifying agent", Gas/Liquid and Liquid/Liquid Interface, Proceedings of the International Congress of Surface Activity, (19570000), pp. 426-438.
I. Erni et al., "Chemical Characterization of Iron(III) Hydroxide-Dextrin Complexes", Arzneim.-Forsch./Drug Res., (19840000), vol. 34, No. II, pp. 1555-1559.
F. Funk et al., "Physical and Chemical Characterization of Therapeutic Iron Containing Materials", Hyperfine Interactions, (20010000), vol. 136, pp. 73-95.
A. John, "Neue Moglichkeiten der Eisenversorgung neugeborener Ferkel unter Beachtung biochemischer Aspekte", Novel possibilities of supplying iron to new born piglets, taking account of biochemical aspects], Trachtigkeit und Geburt beim Schwein [Pregnancy and birth in pigs, (20020000), pp. 89-94.

(Continued)

*Primary Examiner* — Layla D Berry
(74) *Attorney, Agent, or Firm* — McBee Moore & Vanik, IP, LLC

(57) ABSTRACT

The present invention relates to a formulation for use in the simultaneous treatment of coccidial infections and iron deficiencies containing a triazinone such as toltrazuril and a polynuclear iron(III) polysaccharide complex compound together with a specifically selected surfactant that has a hydrophilic-lipophilic-balance (HLB) value of ≥10.

7 Claims, No Drawings

(56) References Cited

OTHER PUBLICATIONS

E. London, "The Molecular Formula and Proposed Structure of the Iron-Dextran Complex, Imferon", J. Pharm. Sci., (20040000), vol. 93, doi:doi:10.1002/jps.20093, pp. 1838-1846.

D.S. Kudasheva et al., "Structure of Carbohydrate-bound Polynuclear Oxyhydroxide Nanoparticles in Parenteral Formulation", J. Inorg. Biochem., (20040000), vol. 98, doi:doi:10.1016/j.jinorgbio.2004.06.010, pp. 1757-1769.

Anja Joachim et al., "Comparison of an injectable toltrazuril-gleptoferron (Forceris ) and an oral toltrazuril (Baycox ) + injectable iron dextran for the control of experimentally induced piglet cystoisosporosis", Parasites & Vectors, (Mar. 27, 2018), vol. 11, No. 1, doi:10.1186/s13071-018-2797-5, XP055613420 [I] 1-13 * p. 2, column I * * p. 6, col. I, lines 4-8, paragraphs 2-3.

Anonymous, "CVMP assessment report for Forceris (EMEA/V/C/004329/0000) International non-proprietary name: toltrazuril/ iron (iii) ion", CVMP Assessment Report for Forceris (EMEA/V/C/004329/0000) EMA/138662/2019, (Feb. 21, 2019), pp. 1-37.

Forceris: EPAR—Product information, May 16, 2019, 19 pages.

Pan Weisan, 'Surfactant and Non-Surfactant Mixing Systems'. Surfactants, Industrial Pharmaceutics, Sep. 5, 2023.

* cited by examiner

FORMULATION FOR THE USE IN THE SIMULTANEOUS TREATMENT OF COCCIDIAL INFECTIONS AND IRON DEFICIENCIES

The present invention relates to a formulation for use in the simultaneous treatment of coccidial infections and iron deficiencies containing a triazinone such as toltrazuril and a polynuclear iron(III) polysaccharide complex compound together with a specifically selected surfactant.

Economically successful meat production operations are currently distinguished by highly intensive farming, that is to say by the keeping of a large number of animals which are specifically selected in order to optimize the breeding aim. These farms are characterized for example by the use of a great deal of machinery, the additional feeding of food supplements, and the involvement of as little staff as possible. In the case of piglet rearing farms, this means that a large number of sows which are bred for a high number of piglets per litter are kept in suitably large pig houses. The optimization of the feed, and suitable selection in the breeding process, make it possible for the piglets to grow rapidly.

This type of animal keeping is frequently the cause for an increasing number of certain typical diseases and deficiencies. Besides stress, to which in particular intensively kept pigs are very susceptible, such phenomena are, in young pigs, protozoal infections (coccidioses) and anaemic states, inter alia, both of which already have to be kept under control by the prophylactic use of medicaments.

Coccidioses are frequently occurring, parasitic infectious diseases in animals. Thus, for example, protozoans of the genera *Eimeria, Isospora, Neospora*, Sarcosporidia and *Toxoplasma* cause coccidioses all over the world. Examples of economically important coccidioses are: infections of pigs with coccidia of the genus *Isospora* or of cattle with coccidia of the genus *Eimeria*. Infections with *Isospora suis* have only in recent years been recognized as the cause of diarrhea in piglets and studied intensively. As a rule, an infection proceeds from the environment to the piglets, or from piglet to piglet, via oocysts, which contain in each case two sporocysts with in each case two sporozoites. The parasitic stages multiply in the epithelial cells of the small intestine's villi. The clinical picture of the disease includes a necrotic, inflammatory destruction of the gut's epithelial cells with atrophying villi, and, as a result, impaired absorption and digestion. The characteristic of an acute disease is a liquid, whitish to yellow diarrhea, which mostly occurs in week 2 to 3 of life. The weight gain of infected piglets is reduced. Treatment and therapy of the disease are insufficient to date.

Antibiotics are ineffective; while sulphonamides are approved for the treatment of coccidiosis, their effect is questionable, and frequently repeated administrations are in any case unsuitable for practice. Other possible treatments are questionable: the administration of, for example, monensin, amprolium or furazolidon has not been successful in preventing the disease in experimentally infected piglets. In more recent studies, *Isospora suis* has been identified in up to 92% of all litters in some farms, despite good hygiene. This type of disease is not limited to pigs, but also occurs in many other animal species, for example in poultry production, in calves, lambs or in small animals (rabbits).

An example of a deficiency is iron deficiency in newly-born piglets. Owing to the rapid growth in the first days after birth, the body's iron reserves are rapidly depleted and must be compensated for by external sources. Because of the large number of suckling pigs, this substitution by taking up the sow's milk cannot take place in a sufficient degree. If, moreover, the animals are kept on concrete or plastic, the piglets cannot take up iron compounds by rooting in the ground either. The piglets become anaemic.

A clinically significant anaemic state exists when the hemoglobin content of the blood has dropped to less than 80 g/l. The NRC recommendation (National Research Council, Nutrient Requirements of Domestic Animals, No. 6, Nutrient Requirements of Swine, National Academy of Sciences, Washington DC, 1979) specifies 90 g/l as the minimum hemoglobin value at which the piglets grow healthily and show no signs of anaemia. Noticeable symptoms such as weight loss or stunted growth are, however, only observed when the hemoglobin content of the blood has dropped to values of below 80 g/l. Other indicators for the iron supply are the hematocrit and the number of erythrocytes per unit volume. Severe iron deficiency anaemia also leads to the young pigs' death.

Preparations are already available for controlling the above-mentioned diseases and deficiencies.

Coccidiosis can be controlled successfully by administering active ingredients from the triazinone group. To this end, one distinguishes between the triazinediones—with examples of representatives being the active ingredients clazuril, diclazuril, letrazuril—and the triazinetriones with the active ingredients toltrazuril, toltrazuril sulphoxide and ponazuril. Triazinones, in particular toltrazuril, ponzazuril or diclazuril, and their activity against coccidia are known from a series of publications, see, inter alia, DE-A 27 18 799 and DE-A 24 137 22.

WO 99/62519 discloses semisolid aqueous preparations of toltrazuril sulphone (ponazuril). It is also known that it is in particular toltrazuril which is suitable for treating coccidiosis (for example *Isospora suis*) in pigs.

The most important compounds on the market in the treatment of coccidiosis are diclazuril (2,6-dichloro-α-(4-chlorophenyl)-4-(4,5-dihydro-3,5-dioxo-1,2,4-triazin-2 (3H)-yl)benzeneacetonitrile; CAS No. 101831-37-2) for admixture to the feed and toltrazuril (1-methyl-3-[3-methyl-4-[4-[(trifluoromethyl)thio]phenoxy]phenyl]-1,3,5-triazine-2,4,6(1H,3H,5H)trione; CAS No. 69004-03-1).

Toltrazuril is available on some markets for example as a drinking water formulation for poultry and as an oral suspension formulation for, inter alia, the treatment of suckling pigs. It is recommended to administer, to the piglet, a dose of 20 mg/kg bodyweight on day 3-5 after birth.

The general concept of combining an active for the treatment of coccidiosis with an iron compound is also known already.

As a matter of best case example, EP 2 164 496 A1 discloses formulations for use in the simultaneous treatment of coccidial infections and iron deficiencies containing a triazinone such as toltrazuril and a polynuclear iron(III) complex compounds and shows the synergism of these two compounds with regard to the clinical endpoint of weight gain of the piglets treatment with such a combination formulation.

EP 2 164 496 A1 also shows that it is not easy to find a formulation that can be built around a triazinone and said polynuclear iron(III) complex compound.

The positive correlation found in EP 2 164 496 A1 has been used for injection use in the disclosure of WO 2014/086958 A1 and WO 2014/086959 A1.

All of the above EP 2 164 496 A1, WO 2014/086958 A1 and WO 2014/086959 A1 inter alia use poly-ω-FeO(OH) type Iron(III) with complex-bound polymeric carbohydrate compounds. It was EP 2 164 496 A1 showing that in the context of combining such polynuclear iron(III) complex compounds with triazine compounds, preference should be given to polynuclear iron(III) polysaccharaide complex compounds.

Within such polynuclear iron(III) polysaccharaide complex compounds, commercial importance has been gained mainly, but not exclusively, by iron(III) dextran (CAS No. 9004-66-4), iron(III) hydroxide polymaltose (iron(III) hydroxide dextrin; CAS No. 53858-86-9), iron(III) sucrose (iron(III) sucrose, iron(III) "sugar" CAS No. 8047-67-4) and sodium/iron(III) gluconate complex in sucrose solution (CAS No. 34089-81-1).

The literature reveals different names for these compounds. In this context, compounds such as Gleptoferron, iron(III) dextran, iron(III) polymaltose, iron(III) dextrin, iron(III) sucrose, iron(III) gluconate, sugar are understood as meaning complexes of the iron(3+) ion with hydroxide ions (OH—), aquo groups ($H_2O$) and oxygen (O), which complexes are present in oligomeric or polymeric form and which are associated, in their coordination sphere, in the form of complexes with one or more of the above-mentioned oligomeric and polymeric carbohydate compounds.

This is why the compounds are also referred to as iron(III) hydroxide polysaccharide or iron(III) oxy-hydroxy polysaccharide, where polysaccharide stands for the above-mentioned oligo- and polymeric carbohydate compounds or their derivatives or, generally, for compounds from the group of the oligomeric or polymeric carbohydrates.

Polynuclear iron(III) complexes of this type are described for example in D. S. Kudasheva et al., "Structure of Carbohydrate-bound Polynuclear Oxyhydroxide Nanoparticles in Parenteral Formulation", J. Inorg. Biochem. 98 (2004) 1757-1769, as well as I. Erni et al., "Chemical Characterization of Iron(III) Hydroxide-Dextrin Complexes" Arzneim.-Forsch./Drug Res. 34 (II) (1984) 1555-1559, F. Funk et al., "Physical and Chemical Characterization of Therapeutic Iron Containing Materials", Hyperfine Interactions 136 (2001) 73-95, E. London "The Molecular Formula and Proposed Structure of the Iron-Dextran Complex, IMFERON", J. Pharm. Sci. 93 (2004) 1838-1846 and A. John "Neue Möglichkeiten der Eisenversorgung neugeborener Ferkel unter Beachtung biochemischer Aspekte" [Novel possibilities of supplying iron to new born piglets, taking account of biochemical aspects], Trächtigkeit und Geburt beim Schwein [Pregnancy and birth in pigs]: 8th Bernburger Biotechnology Workshop, Bernburg (2002) 89-94.

Since in many cases the composition of these compounds is not described in quantitative terms, and may also vary within the compounds, depending on the type of preparation, these polynuclear iron(III) polysaccharide complex compounds are understood as meaning all complexes of the above-described class of compounds which are known to the skilled worker.

These iron compounds are used almost exclusively in the manufacture of preparations for injection for human and veterinary medicine. In veterinary medicine, additionally, a few preparations for oral administration are also in use.

Besides from the first disclosed benefit of combining a triazine compound with an polynuclear iron(III) complex compounds according to EP 2 164 496 A1, there are other potential parameters that may further influence the efficacy and usefulness of a formulation for use in the simultaneous treatment of coccidiosis and iron deficiencies.

As a matter of example, WO 2014/086960 A1 discloses that the formation of foam is obviously an undesirable feature for any formulation. Therefore, WO 2014/086960 A1 teaches that—to avoid excessive formation of foam—aqueous suspensions comprising a triazine, an iron complex, and one or more surfactant(s) having a particularly low HLB value, should be used.

While WO 2014/086960 A1 acknowledges that other surfactants may be used in combination with those of a low HLB value may be added to the respective formulation, WO 2014/086960 A1 does not disclose any reason or threshold with regard to said other surfactants, other than that they have an HLB value higher than those that according to WO 2014/086960 A1 diminish foam formation.

A high HLB surfactant according to the disclosure of WO 2014/086960 A1 is any surfactant that has a HLB higher than 8, while those surfactants that were found to be advantageous of inhibiting foam formation are those that have a HLB of up to 8.

In conclusion, the surfactants of WO 2014/086960 A1 are divided in those that are beneficial to inhibit foam formation and have a HLB of 8 or lower, and those that may or not may not be present that do not have such property.

Surfactants mentioned in WO 2014/086960 A1 that have a high HLB and thus do not contribute to the effect of inhibiting foam formation are polyethylene castor oil derivatives, polyoxyethylene alkyl ether, polyoxyethylene sorbitan fatty acid esters, polyoxyethylene stearate, sodium lauryl sulfate, sodium docusate, cetrimide, phospholipids, or cethylpyridinium chloride.

Such list of alleged high HLB value surfactants is however not specific enough to derive any actual surfactant therefrom that would in reality have such high HLB value per se. As a matter of example, any of the above referred and disclosed polyoxyethylene comprising compounds would only meet the limitation of having a high HLB value, if such would have a sufficiently long polyoxyethylene portion, rendering it more hydrophilic and thus resulting in a higher HLB value.

Further, the disclosed phospholipids usually do not even have a calculable HLB value at all, and if so it would usually be significantly below 10. That may also form the reason why lecithin (being a phospholipid) is mentioned in WO 2014/086960 A1 both as low HLB and high HLB value surfactant.

From those structural classes of potential high HLB surfactants only two specific members are found in the later examples and specifically disclosed formulations of WO 2014/086960 A1.

Those are polyethylene castor oil derivatives which are specified to be Copolymer Polyoxyl 35-hydrogenated castor oil and sodium docusate. WO 2014/086960 A1 discloses 14 individual formulations explicitly, showing the impact on foam formation at different time points and another three explicit formulations that are not specified with regard to the implication thereof on the avoidance of foam formation (page 18, lines 13-22).

With regard to the 14 exemplified formulations, Examples 4, 5, 7 and 8 comprise the surfactant Copolymer Polyoxyl 35-hydrogenated castor oil as a high HLB surfactant, which is sold for instance as Cremophor EL (CAS 61791-12-6), and Examples 9 to 14 comprise sodium docusate as a surfactant.

With regard to the specifically mentioned formulations on page 18 of WO 2014/086960 A1 that are not tested for foam formation, the first two ones comprise Copolymer Polyoxyl 35-hydrogenated castor oil, and the third one is disclosed to comprise sodium docusate.

Sodium docusate has a HLB of about 10 according to US 2014/0127320 A1, while Cremophor EL has a HLB of 12-14 according to the supplier data thereof.

Considering the Examples 9 to 14 of WO 2014/086960 A1 that comprise sodium docusate, it's apparent that those are comparative examples, as none thereof comprise a surfactant that has a HLB of 8 or below being argued to be causative for the inhibition of foam formation.

This is evidenced by the fact that all of the formulations in examples 9 to 14 show excessive foam formation (at least at t=0 min.).

Considering Examples 4, 5, 7 and 8, those formulations comprise either Sorbitan Monooleate, which is also known as SPAN 80 (CAS 1338-43-8) and has a HLB of about 4.6 (Examples 4, 5 and 8) or Propylene Glycol Monolaurate (CAS 27194-74-7) which has a HLB value of about 4.3 to 4.5 (Example 7) pursuant to the intended prevention of foam.

Other than the intended effect of inhibited foam formation by adding either Sorbitan Monooleate or Propylene Glycol Monolaurate as surfactants having a HLB value of about 4.6 or 4.3 to 4.5 respectively, no reference is made to any effect that could or would be attributed to the further addition of Copolymer Polyoxyl 35-hydrogenated castor oil, having a HLB of from 12 to 14.

According to WO 2014/086960 A1 another alleged low HLB surfactant that is deemed preferred is a simethicone emulsion, while said simethicone emulsion is not sufficiently specified in WO 2014/086960 A1 to retrieve a HLB value that could be assigned to it. The disclosure of WO 2014/086960 A1 is also unclear whether said simethicone emulsion is in fact really to be considered to fall under the definition of a low HLB surfactant as to WO 2014/086960 A1, while it is clearly taught from WO 2014/086960 A1 that addition of simethicone emulsion is beneficial to avoid foam formation.

Simethicone is per se a mixture of $\alpha$-(trimethylsilyl)-$\omega$-methylpoly[oxy(dimethylsilylene)] with silicon dioxide of—at least with regard to WO 2014/086960 A1—unspecified ratio of those two compounds and the disclosed emulsion is also not disclosed more specifically.

There is no indication of the solvent or dispersant of the mixture of $\alpha$-(trimethylsilyl)-$\omega$-methylpoly[oxy(dimethylsilylene)] with silicon dioxide to form said emulsion, neither any indication on any further additives to such emulsion to remain an emulsion. This implies that the beneficial effect of having said simethicone emulsion in the formulations pursuant to WO 2014/086960 A1 is rather derived from the unknown surfactant required to stabilize the emulsion than by the silicon dioxide or $\alpha$-(trimethylsilyl)-$\omega$-methylpoly[oxy(dimethylsilylene)] itself.

Therefore, the implication of the preferred addition of simethicone (emulsion) to the formulations disclosed in WO 2014/086960 A1 remains unclear, particularly in view of Examples 9 to 14.

The specific formulations disclosed in of WO 2014/086960 A1 that also comprise a surfactant with a HLB value of more than 8 are more specifically those listed hereunder.

Example 4 describes a formulation, consisting of 3.5% toltrazuril, 17.8% of iron (as Gleptoferron), 0.3% of sorbitan monooleate, 10% diethylene glycol monoethyl ether, 0.1% of copolymer Polyoxyl 35-hydrogenated castor oil, and Water ad 100%.

Example 5 describes a formulation, consisting of 3.5% toltrazuril, 19.4% of iron (as Gleptoferron), 0.3% of sorbitan monooleate, 0.1% of copolymer Polyoxyl 35-hydrogenated castor oil, and Water ad 100%.

Example 7 describes a formulation, consisting of 3.5% toltrazuril, 19.3% of iron (as Gleptoferron), 0.3% of Propylene Glycol Monolaurate, 0.1% of copolymer Polyoxyl 35-hydrogenated castor oil, 1% Sodium Chloride, and Water ad 100%.

Example 8 describes a formulation, consisting of 3.5% toltrazuril, 19.4% of iron (as Gleptoferron), 0.3% of sorbitan monooleate, 0.1% of copolymer Polyoxyl 35-hydrogenated castor oil, and Water ad 100%.

Example 9 describes a formulation, consisting of 4.2% toltrazuril, 13.5% of iron (as Gleptoferron), 0.1% Sodium Docusate, 0.1% silicone emulsion, 1.5% sodium chloride, and Water ad 100%.

Example 10 describes a formulation, consisting of 4.2% toltrazuril, 13.5% of iron (as Gleptoferron), 0.1% Sodium Docusate, 5% diethylene glycol monoethyl ether, 0.1% silicone emulsion, 1% sodium chloride, and Water ad 100%.

Example 11 describes a formulation, consisting of 4.2% toltrazuril, 13.5% of iron (as Gleptoferron), 0.6% Phenole, 0.2% Sodium Docusate, 0.1% simethicone emulsion USP 30%, 0.5% colloidal silicone dioxide, 1% povidone, 0.5% sodium chloride, and Water ad 100%.

Example 12 describes a formulation, consisting of 4.2% toltrazuril, 13.5% of iron (as Gleptoferron), 0.6% Phenole, 0.2% Sodium Docusate, 0.1% simethicone emulsion USP 30%, 0.5% colloidal silicone dioxide, 1% povidone, 1% sodium chloride, and Water ad 100%.

Example 13 describes a formulation, consisting of 4.2% toltrazuril, 13.5% of iron (as Gleptoferron), 0.6% Phenole, 0.1% Sodium Docusate, 0.1% simethicone emulsion USP 30%, 0.5% colloidal silicone dioxide, 1% povidone, 1% sodium chloride, and Water ad 100%.

Example 14 describes a formulation, consisting of 2.9% toltrazuril, 18.8% of iron (as Gleptoferron), 0.6% Phenole, 0.1% Sodium Docusate, 0.1% simethicone emulsion USP 30%, 0.5% colloidal silicone dioxide, 1% povidone, 1% sodium chloride, and Water ad 100%.

The three explicitly mentioned formulations given on page 18 of WO 2014/086960 A1 consist of 2.9% toltrazuril, 18.8% of iron (as Gleptoferron), 0.3% of sorbitan monooleate, 0.1% of copolymer 15 Polyoxyl 35-hydrogenated castor oil, 1.5% of sodium chloride and water, or 4.2% toltrazuril, 13.5% of iron (as Gleptoferron), 0.3% of sorbitan monooleate, 0.1% of copolymer Polyoxyl 35-hydrogenated castor oil, 1.5% of sodium chloride and water, or 4.2% toltrazuril, 13.5% of iron (as Gleptoferron), 1% of sodium chloride, 1% of polyvinylpyrrolidone, 0.6% of phenol, 0.5% of colloidal silicon dioxide, 0.1% of sodium docusate, 0.1% of simethicon emulsion and water.

WO 2014/086960 A1 generically discloses that any of the formulations described are suitable to treat animals against coccidiosis, but fails to disclose that simultaneous treatment of coccidiosis and anemia is pursued and further fails to disclose with regard to those specific formulations mentioned in Examples 4, 5, 7, 8, 9 to 14 and on page 18 that these may be particularly suitable for that simultaneous treatment purpose.

Departing from the above referred to prior art, several problems associated with objective of providing with suitable simultaneous treatment options for coccidiosis and anemia have been addressed.

More specifically, the problem of providing with a synergy between a triazinone compound and an iron complex compound has been found and addressed in EP 2 164 496 A1, and the problem of foam formation has been found and addressed in WO 2014/086960 A1 in adding surfactants to the combination of triazinone and iron complex compound that have a HLB value below 8.

Departing from that, it has now been surprisingly been found that the advantageous effects found in EP 2 164 496 A1 can be further improved by selecting appropriate surfactants that foster the synergy between certain triazinone compounds and certain iron (III) complex compounds.

Accordingly in a first aspect of the present invention a formulation is provided for use in the simultaneous treatment of coccidial infections and iron deficiencies in non-human animals, the formulation comprising toltrazuril or diclazuril, a polynuclear iron(III) polysaccharide complex compound and at least one surfactant having a HLB value of 10 or more.

None of the above discussed prior art reference indicates that addition of at least one surfactant having a HLB value of 10 or more may be beneficial to the efficacy of any of the actives of such formulations.

It is of advantage to combine the aforementioned treatments of anemia and coccidiosis into a single treatment. It eases the stress for the animals, improves animal welfare and reduces handling efforts and personnel input in commercial farms, providing an economical advantage. In the end—as first proven by EP 2 164 496 A1—such combination results in improved weight gain of the animals treated.

It is of further advantage if a reduction in the exposure of animals and environment to the active substances and its metabolites could be achieved, i.e. by reducing the dose, without a loss of efficacy, which can be further improved pursuant to the present invention.

In a second aspect of the present invention, a formulation is provided for use in the simultaneous treatment of coccidial infections and iron deficiencies in non-human animals, the formulation comprising toltrazuril or diclazuril, a polynuclear iron(III) polysaccharide complex compound and at least one surfactant having a HLB value of 10 or more, with the exception of the formulations that are disclosed in Examples 4, 5, 7 and 8 of WO 2014/086960 A1.

In said second aspect of the invention, formulations for use in the simultaneous treatment of coccidial infections and iron deficiencies in non-human animals, the formulation comprising toltrazuril or diclazuril, a polynuclear iron(III) polysaccharide complex compound and at least one surfactant having a HLB value of 10 or more, with the exception of formulations comprising Copolymer Polyoxyl 35-hydrogenated castor oil as a surfactant, when toltrazuril is used, are preferred.

In a third aspect of the present invention, a formulation is provided for use in the simultaneous treatment of coccidial infections and iron deficiencies in non-human animals, the formulation comprising toltrazuril or diclazuril, a polynuclear iron(III) polysaccharide complex compound and at least one surfactant having a HLB value of 10 or more, with the exception of the formulations that are disclosed in Examples 9 to 14 of WO 2014/086960 A1.

In said third aspect of the invention, formulations for use in the simultaneous treatment of coccidial infections and iron deficiencies in non-human animals, the formulation comprising toltrazuril or diclazuril, a polynuclear iron(III) polysaccharide complex compound and at least one surfactant having a HLB value of 10 or more, with the exception of formulations comprising sodium docusate as a surfactant, when toltrazuril is used, are preferred.

In a fourth aspect of the present invention, a formulation is provided for use in the simultaneous treatment of coccidial infections and iron deficiencies in non-human animals, the formulation comprising toltrazuril or diclazuril, a polynuclear iron(III) polysaccharide complex compound and at least one surfactant having a HLB value of 10 or more, with the exception of the formulations that are disclosed in Examples 4, 5, 7, 8, 9 to 14 of WO 2014/086960 A1 as well as formulations consisting of those mentioned on page 18 of WO 2014/086960 A1.

As outlined just above the thereby excepted formulations that are disclosed in WO 2014/086960 A1 unwantedly comprise surfactants of a HLB value of 10 or more, while actually wanting to achieve inhibition of foam formation by virtue of surfactants having a HLB value below 8.

In any of the above referred to aspects of the invention, formulations for use in the simultaneous treatment of coccidial infections and iron deficiencies in non-human animals, the formulation comprising toltrazuril or diclazuril, a polynuclear iron(III) polysaccharide complex compound and at least one surfactant having a HLB value of 10 or more, with the further exception of a formulation consisting of 5% toltrazuril, 22.8% Iron in the form of Fe(III)dextrane, 0.2% sodium proprionate, 0.2% sodium benzoate, 0.25% sodium docusate, 0.05% simethicone emulsion USP 30%, 10.5% propylene glycole, 1.03% citric acid, 0.15% bentonite and water ad. 100% are preferred.

In the context of the present invention it has however been found that due the addition of said surfactant of a HLB value of 10 or more, any dose of—particularly—toltrazuril (or diclazuril) may be lowered due to a double synergy between toltrazuril (or diclazuril) and the polynuclear iron(III) polysaccharide complex compound as well as between those and the surfactant of a HLB value of or more.

Surprisingly, it was found that pharmacokinetic parameters as the area under the curve (AUC) and $C_{max}$ were increased when toltrazuril (or diclazuril) was administered into rats together with surfactants of a HLB of 10 or more. Said effect on AUC and $C_{max}$ is also found when toltrazuril (or diclazuril) is co-administered with a polynuclear iron(III) polysaccharide complex compound such as iron dextran or iron dextran glucoheptonate.

Very surprisingly the unknown advantage of the addition of a surfactant of a HLB of 10 or more dramatically stacks with the effect on AUC and $C_{max}$ found when combining said surfactant administration with a co-administration of toltrazuril or diclazuril and a polynuclear iron(III) polysaccharide complex compound in pigs.

This constitutes an advantage since it demonstrates dramatically increased bioavailability in those combination formulations in comparison to simple toltrazuril (or diclazuril) or combined toltrazuril (or diclazuril) and polynuclear iron(III) polysaccharide complex compound formulations.

As a consequence a reduction of dose, compared to marketed commercial or disclosed toltrazuril (or diclazuril) or combined toltrazuril (or diclazuril) and polynuclear iron (III) polysaccharide complex compound formulations, may be possible.

Said advantage is independent on the route of administration. It can be shown that parenteral—particularly injection—and oral administration according the present invention result in the same advantage.

In the context of the present invention the HLB value is either determined according to the method of Davies (Davies J T (1957), "A quantitative kinetic theory of emulsion type, I. Physical chemistry of the emulsifying agent", Gas/Liquid and Liquid/Liquid Interface, Proceedings of the International Congress of Surface Activity, pp. 426-38) or according to the method of Griffin (Griffin W C (1954), "Calculation of HLB values of non-ionic surfactants", Journal of the Society of Cosmetic Chemists, pp. 249-56).

Both methods correlate the hydrophilic-lipophilic-balance (HLB) value with the chemical nature of a molecule on the basis of semi-empirical equations that show a correlation between the amount of hydrophobic parts of a molecule compared to the amount of hydrophilic parts of said molecule that is considered to be a surfactant.

Both methods result in similar, but not identical HLB values, as far as non-ionic surfactants are concerned. Usually, non-ionic surfactants more commonly get assigned an HLB value according to Griffin.

Therefore, in the context of the present invention, pertaining to the addition of a surfactant of a HLB value of ≥10, the deviations of resulting HLB value between those from the formula of Davies or Griffin, are not essential, as they usually do not produce discrepancies exceeding a deviation of more than ±1 when applied to non-ionic surfactants.

Another class of surfactants is phospholipids. Within said class, phosphatidylcholines which are so called zwitter-ionic surfactants need to be addressed separately. The respective HLB value thereof significantly depends on their actual composition and degree of purity. As a matter of example, crude soy lecithin has a HLB value of 3, while purified soy phosphatidylcholine has a HLB value of about 7 (see Gunstone F D, "Lipid Technologies and Applications" (1997) p. 62, Table 10).

Apparently their respective HLB values are rather empirically derived than calculated from either of the above formulas.

Accordingly, any HLB value mentioned in the context of the present invention can be derived either from Davies or Griffin or otherwise determined and the value thus must be understood as the value stated±1. In any event the HLB values relevant to the present invention to work, do not overlap with those according to WO 2014/086960 A1, only specified to be calculated according to Davies, and relevant to avoid excessive foam formation.

The at least one surfactant with a hydrophilic-lipophilic-balance (HLB) value of ≥10 ("high HLB value surfactant") according to the present invention, preferably has a HLB value of ≥10 to ≤18, more preferred ≥10 to ≤16.7.

Preferred surfactants with a HLB value of ≥10 are those selected from the list of Sodium Docusate (HLB 10), Polysorbates, Copolymer Polyoxyl 35-hydrogenated castor oil (HLB 12-14), Pluronic F-68 (HLB 29) and Vitamin E TPGS (HLB 13.2).

Amongst the Polysorbates, Polysorbate 20 (HLB 16.7) and Polysorbate 80 (HLB 15) are preferred.

More preferred surfactants with a HLB value of ≥10 are those selected from the list of Sodium Docusate, Polysorbate 20 and Polysorbate 80.

Even more preferred surfactants with a HLB value of ≥10 are those selected from the list of Polysorbate 20 and Polysorbate 80.

In a further preferred embodiment of all above referred to aspects of the invention more than one surfactant with a HLB value of ≥10 is present in the formulation.

Within said further preferred embodiment at least two surfactants with a HLB value of ≥10 are present in the formulation, of those at least two, two preferably being Polysorbate 20 (HLB 16.7) and Polysorbate 80 (HLB 15).

In the present context, polynuclear iron(III) polysaccharide complex compounds are understood as meaning complexes of the iron(3+) ion with hydroxide ions (OH—), aquo groups ($H_2O$) and oxygen (O) which are present in oligomeric or polymeric form and which are associated in their coordination sphere as complexes with one or more than one of the above oligomeric and polymeric carbohydrate compounds. This is why the compounds are also referred to as iron(III) hydroxide polysaccharide or iron(III) oxyhydroxy polysaccharide, where polysaccharide represents the corresponding oligomeric and polymeric carbohydrate compounds or their derivatives.

Polynuclear iron(III) complexes of this type are described for example in (D. S. Kudasheva et al., "Structure of Carbohydrate-bound Polynuclear Oxyhydroxide Nanoparticles in Parenteral Formulation", J. Inorg. Biochem. 98 (2004) 1757-1769; I. Erni et al "Chemical Characterization of Iron(III) Hydroxide-Dextrin Complexes" Arzneim.-Forsch./Drug Res. 34 (II) (1984) 1555-1559; F. Funk et al., "Physical and Chemical Characterization of Therapeutic Iron Containing Materials", Hyperfine Interactions 136 (2001) 73-95; E. London "The Molecular Formula and Proposed Structure of the Iron-Dextran Complex, IMFERON", J. Pharm. Sci. 93 (2004) 1838-1846; A. John "Neue Möglichkeiten der Eisenversorgung neugeborener Ferkel unter Beachtung biochemischer Aspekte" [Novel possibilities of supplying iron to new born piglets, taking account of biochemical aspects], Trächtigkeit und Geburt beim Schwein [Pregnancy and birth in pigs]: 8th Bernburger Biotechnology Workshop, Bernburg (2002) 89-94).

Since in many cases the precise composition of these compounds is not described in quantitative terms, and may also vary within the compounds, depending on the type of preparation, these polynuclear iron(III) polysaccharide complex compounds are understood as meaning all compounds which the skilled worker ascribes to this class of compounds.

Examples of polynuclear iron(III) polysaccharide complex compounds may be mentioned are: polynuclear iron (III) polysaccharide complex compounds in which a polynuclear D-FeO(OH) nuclear complex contains polymeric carbohydrate compounds associated at the free coordination sites, for example Gleptoferron, iron(III) dextran, iron(III) hydroxy polymaltose (iron(III) dextrin), nonstoichiometric compounds of D-FeO(OH) with saccharides and oligosaccharides "iron(III) sucrose" "iron(III) 'sugar'".

The formulation used according to the invention can be a solution, emulsion or suspension.

Solutions are prepared by dissolving the active ingredient, or active ingredients, in suitable solvents or solvent mixtures. If appropriate, further adjuvants such as solubilizers, antioxidants, preservatives, thickeners, adhesives, pH regulators, UV stabilizers or colorants are added.

Solvents which may be mentioned are: physiologically acceptable solvents such as water, alcohols, such as, for example, monohydric alkanols (for example ethanol or n-butanol), polyhydric alcohols such as glycols (for example ethylene glycol, propylene glycol, tetraglycol/glycofurol), polyethylene glycols, polypropylene glycols, glycerol; aromatically substituted alcohols such as benzyl alcohol, phenylethanol, phenoxyethanol; esters such as ethyl acetate, butyl acetate, benzyl benzoate, ethyl oleate; ethers such as alkylene glycol alkyl ethers (for example dipropylene glycol monomethyl ether, diethylene glycol monobutyl ether); ketones such as acetone, methyl ethyl ketone; aromatic and/or aliphatic hydrocarbons, vegetable or synthetic oils; glycerol formal, solketal (2,2-dimethyl-4-hydroxymethyl-1, 3-dioxolane), N-methylpyrrolidone, 2-pyrrolidone, N,N-dimethylacetamide, glycofurol, dimethylisosorbitol, lauroglycol, propylene carbonate, octyldodecanol, dimethylformamide, and mixtures of the above-mentioned solvents.

Water is preferred as a solvent and/or suspension medium.

Solubilizers which may be mentioned are agents which promote the dissolution of the active ingredient in the main solvent or which prevent its precipitation. Examples for agents that prevent precipitation are polyvinylpyrrolidones.

Antioxidants are sulphites or metabisulphites such as potassium metabisulphite or sodium metabisulphite, sodium disulphite or potassium disulphite, ascorbic acid, isoascorbic acid, ascorbyl palmitate, gallic acid esters, butylhydroxytoluene, butylhydroxyanisole or tocopherols.

Synergists of these antioxidants may be: amino acids (for example alanine, arginine, methionine, cysteine), citric acid, tartaric acid, edetic acid or their salts, phosphoric acid derivatives or polyalcohols (polyethylene glycol).

Preservatives may be: benzyl alcohol, benzalkonium chloride, trichlorobutanol, p-hydroxybenzoate, n-butanol, chlorocresol, cresol, phenol, benzoic acid, citric acid, tartaric acid or sorbic acid.

Thickeners may be: inorganic thickeners such as bentonites, colloidal silica, aluminium stearates, organic thickeners such as cellulose derivatives, for example Hydroxypropylmethylcellulose 4000, polyvinyl alcohols and their copolymers, xanthan, acrylates and methacrylates, carboxymethylcellulose and its salts.

Adhesives are, for example, cellulose derivatives, starch derivatives, polyacrylates, natural polymers such as alginates, gelatin.

Adhesives which also have thickening properties may likewise be employed as thickeners. pH regulators are pharmaceutically customary acids or bases. The bases include alkali metal hydroxides or alkaline earth metal hydroxides (for example NaOH, KOH), basic salts such as, for example, ammonium chloride, basic amino acids such as, for example, arginine, choline, meglumine, ethanolamines or else buffers such as tris(hydroxymethyl)aminomethane, citric acid buffers or phosphate buffers. The acids include, for example, hydrochloric acid, acetic acid, tartaric acid, citric acid, lactic acid, succinic acid, adipic acid, methanesulphonic acid, octanoic acid, linolenic acid, gluconolactone, and acidic amino acids such as, for example, aspartic acid.

UV stabilizers are, for example, substances from the class of the benzophenones, or novantisolic acid.

Colorants are all colorants which are approved for use on humans or animals and which may be dissolved or suspended.

Suspensions are prepared by suspending the active ingredient, or active ingredients, in a carrier liquid, if appropriate, with addition of further auxiliaries (in addition to the aforementioned surfactants) such as wetters, colorants, absorption accelerators, thickeners, dispersants, adhesives, preservatives, antioxidants, UV stabilizers or antifoams.

The formulations used according to the invention are preferably "water based".

This means that, as a rule, they contain from ≥10 to 90% by weight, preferably from ≥20 to ≤80% by weight, especially preferably from ≥30 to ≤50% by weight of water.

For example, the formulations as mentioned above may comprise further water-miscible solvents. Further water-miscible solvents which may be mentioned by way of example are preferably polyhydric aliphatic alcohols such as ethylene glycol, diethylene glycol, triethylene glycol, propylene glycol and glycerol; among these, propylene glycol is especially preferred.

Such further water-miscible solvents are usually present in concentrations of from ≥1 to ≤45% by weight, preferably from ≥1 to ≤20% by weight, especially preferably from ≥5 to ≤10% by weight. The addition of such polyhydric aliphatic alcohols also has the advantage of lowering the freezing point of the formulation.

The formulations used according to the invention as stated above can furthermore contain preservatives, if appropriate in combination with what are known as synergists. The preservatives are usually present in concentrations of from ≥0.01 to ≤5% by weight and specifically of ≥0.05 to ≤1% by weight.

If required, antioxidants which may be employed in the used formulations mentioned are, preferably, BHA or BHT. To ensure a sufficient preservation, the preservatives may be employed singly or else in combination with what are known as synergists. Synergists such as citric acid, tartaric acid, ascorbic acid or the sodium salt of editic acid are usually present in concentrations of from ≥0.01 to ≤1% by weight, specifically of ≥0.05 to ≤0.15% by weight.

The formulations used according to the invention are preferably prepared by initially introducing the solvent, preferably water, and pre-dissolving or dispersing therein if appropriate auxiliaries and/or additives such as, for example, co-solvents, preservatives, antioxidants and viscosity-regulating additives.

In the preferred method, a second step involves introducing, into this initial solution, toltrazuril or diclazuril, optionally in the form of a ready-made dispersion concentrate, using a powerful homogenizer and homogenizing the mixture until the finely divided suspension is obtained.

Then, the iron compound, preferably in the form of a powder, is introduced into this dispersion, during which process the mixture is again homogenized. In the last step, finally, the desired pH is adjusted by addition of suitable pH regulators. Individual or all auxiliaries and/or additives may, if appropriate, also be added after the last homogenization step; this may be advisable for example in the case of certain thickeners, whose structure is destroyed by the homogenization process.

As outlined with the above referred to aspects of the present invention the formulations according to the invention are intended for use in the combined control of Coccidia and iron deficiencies, in particular in animals.

Said use facilitates simple and simultaneous administration of the anticoccidial toltrazuril or diclazuril and iron.

Use can be made in animal keeping and animal breeding in livestock, breeding animals, zoo animals, laboratory animals, experimental animals and pets. The spectrum of action of toltrazuril or diclazuril is, in principle, well known. Coccidia which may be mentioned individually are:

*Mastigophora* (*Flagellata*) such as, for example, Trypanosomatidae, for example *Trypanosoma brucei, T. gambiense, T. rhodesiense, T. congolense, T. cruzi, T. evansi, T. equinum, T. lewisi, T. percae, T. simiae, T. vivax, Leishmania brasiliensis, L. donovani, L. tropica*, such as, for example, Trichomonadidae, for example *Giardia lamblia, G. canis*.

Sarcomastigophora (*Rhizopoda*) such as, for example, Entamoebidae, for example *Entamoeba histolytica*, Hartmanellidae, for example *Acanthamoeba* sp., Hartmanella sp.

Apicomplexa (Sporozoa) such as, for example, Eimeridae, for example *Eimeria ascervulina, E. adenoides, E. alabahmensis, E. anatis, E. anseris, E. arloingi, E. ashata, E. auburnensis, E. bovis, E. brunetti, E. canis, E. chinchillae, E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra, E. spec., E. stiedai, E. suis, E. tenella, E. truncata, E. truttae, E. zuernii, Globidium* spec., *Isospora belli, I. canis, I. felis, I. ohioensis, I. rivolta, I. spec., I. suis, Neospora caninum, N. hugesi, Cystisospora spec., Cryptosporidium spec.* such as, for example, Toxoplasmadidae, for example *Toxoplasma gondii*, such as, for example, Sarcocystidae, for example *Sarcocystis bovicanis, S. bovihominis, S. neurona, S. ovicanis, S. ovifelis, S. spec., S. suihominis* such as, for example, Leucozoidae, for example *Leucozytozoon simondi*, such as, for example, Plasmodiidae, for example *Plasmodium berghei, P. falciparum, P. malariae, P. ovale, P. vivax, P. spec.*, such as, for example, Piroplasmea, for example *Babesia argentina, B. bovis, B. canis, B. spec., Theileria parva, Theileria spec.*, such as, for example, Adeleina, for example *Hepatozoon canis, H. spec.*

Furthermore *Myxospora* and *Microspora*, for example *Glugea spec., Nosema spec.*

Furthermore *Pneumocystis carinii*, and also *Ciliophora (Ciliata)* such as, for example, *Balantidium coli, Ichthiophthirius spec., Trichodina spec., Epistylis spec.*

Those genera and species of protozoans which lead to subclinical or clinical infections in pigs must be very particularly emphasized, especially: *Eimeria debliecki, E. suis, E. scabra, E. perminuta, E. spinosa, E. polita, E. porci, E. neodebliecki, Isospora suis, Cryptosporidium, Toxoplasma gondii, Sarcocystis miescheriana, S. suihominis, Babesia trautmanni, B. perroncitoi, Balantidium coli.*

Livestock and breeding animals to which the use of the formulation according to the invention is of particular benefit include mammals such as, for example, cattle, horses, sheep, pigs, goats, camels, water buffalos, donkeys, rabbits, fallow deer, reindeer, fur-bearing animals such as, for example, mink, chinchilla, raccoon, birds such as, for example, chickens, geese, turkeys, ducks, pigeons, ostriches, bird species which are kept as companion animals and as zoo animals. They furthermore include farmed fish and ornamental fish.

In this context, pigs, cattle, sheep and dogs of all species, subspecies and breeds may be particularly emphasized.

Laboratory and experimental animals include mice, rats, guinea pigs, golden hamsters, dogs and cats. Pets include dogs and cats.

The use in pigs is especially preferred.

The formulations used according to the invention may contain further active ingredients or components—singly or in suitable combinations —, such as, for example, nutrients, which include, for example, vitamins, minerals, and phosphorus compounds which are suitable as metabolic and immune stimulants:

Vitamins such as, for example, vitamin E, vitamins from the B series such as, for example, vitamin B12, vitamin C. Some of the above may act as surfactants as well.

Minerals, preferably calcium or magnesium salts, in particular for example calcium gluconate, calcium glucoheptanoate or calcium saccharate.

Phosphorus compounds, in particular pharmacologically acceptable organic phosphonic acid derivatives which are suitable as metabolic stimulants and tonics. Preferred examples which may be mentioned are the compounds toldimfos and, in particular, butaphosphane, which have already been known for a long time.

As the result of the poor solubility of toltrazuril or diclazuril, the latter are frequently present, in the formulations used according to the invention, in finely divided form.

Here, the dispersed toltrazuril or diclazuril preferably has a particle size (measured by laser diffraction, Malvern Mastersizer® 2000) of d(v,90)<30 µm, preferably d(v,90) <20 µm, especially preferably d(v,90)<10 µm, and very especially preferably d(v,90) 7 µm or less.

For the purposes of the present invention, d(v,90) is to be understood as meaning a volume-related particle size distribution where 90% of all particles have a dimension (diameter) of this value or less. Usually, this information is referred to as d(90), but the more precise term d(v,90) may be chosen in order to make clear that it is a volume-related particle size distribution. The names d(v,50), d(v,10) and the like are to be understood correspondingly. The particle sizes indicated here were determined with the laser diffraction method using the Mastersizer 2000 apparatus (dispersing unit Hydro 2000G) from Malvern and using the Fraunhofer diffraction evaluation mode since the refractive indices of the active ingredient particles are not known. Here, a suitable amount of the sample solution is predispersed, with stirring, with 2-3 ml of a dispersion medium (0.1% aqueous dioctyl sodium sulphosuccinate solution). The dispersion is then placed into the dispersing unit of the apparatus, with stirring (300 rpm) and recirculating (900 rpm), where it is measured. The evaluation software gives the particle size as d(0.5), d(0.9) values and the like.

In a preferred embodiment of the present invention the formulation is for use at a dosage regimen of 1 to 60 mg toltrazuril or diclazuril per kg bodyweight (mg/kg) of the animal to be treated per day.

In said preferred embodiment the dosage regimen is preferably of 10 to 40 mg toltrazuril or diclazuril per kg bodyweight (mg/kg) of the animal, more preferably of 10 to 20 mg/kg per day, most preferably of about 20 mg/kg per day.

In the most preferred embodiment the above referred to dosage regimen is used only once.

In another preferred embodiment of the present invention the formulation is for use at a dosage regimen of 100 to 300 mg polynuclear iron(III) polysaccharide complex compound.

In said preferred embodiment the dosage regimen is preferably of 150 to 250 mg polynuclear iron(III) polysaccharide complex compound per kg bodyweight (mg/kg) of the animal, more preferably of about 200 mg/kg per day.

As the present invention particularly relates to the combined use of the above toltrazuril or diclazuril and polynuclear iron(III) polysaccharide complex compound, any dosage regimens individually mentioned just above, are preferably combined, with a particular preference to a dosage regimen of about 20 mg/kg per day of toltrazuril or diclazuril and about 200 mg/kg per day of polynuclear iron(III) polysaccharide complex compound.

In a very preferred embodiment the formulation is for use at a dosage regimen of about 20 mg/kg per day of toltrazuril or diclazuril and about 200 mg/kg per day of polynuclear iron(III) polysaccharide complex compound, whereby use is made only on one day. Within said very preferred embodiment, use on day 2 or 3, preferred on day 3 of the life of the animal, preferentially being a piglet is particularly preferred.

The amount of formulation used per administration depends on how much toltrazuril or diclazuril and polynuclear iron(III) polysaccharide complex compound are to be administered in each case.

One aims at relatively small volumes which can be applied readily and which vary depending on the animal species; for sucking pigs, for example, one aims at application volumes of from ≥0.3 to ≤2 ml, preferably from ≥0.5 to ≤1 ml.

Especially preferred formulations according to the invention permit the parenteral treatment of piglets in such a way that a sufficient supply of the piglets with iron in the first four weeks of life can be achieved with a single administration of from ≥0.7 ml to ≤1.3 ml, preferably from ≥0.7 to ≤1.0 ml, of the formulation, even on the third day after birth, where a hemoglobin value of at least ≥8 g/100 ml blood, preferably of more than ≥9 g/100 ml blood, may be considered the indicator for a sufficient supply. In addition, the toltrazuril or diclazuril portion is intended to successfully control coccidia.

In another embodiment the formulation used contains ≥0.1% (m/v) to ≤30% (m/v) of toltrazuril or diclazuril. This corresponds to ≥1 to ≤300 mg/ml. Preferred are ≥1.5 to ≤25% (m/v), corresponding to ≥15 to ≤250 mg/ml, especially preferably ≥1.8 to ≤15% (m/v), corresponding to ≥18 to ≤150 mg/ml, in particular ≥1.8 to ≤7% (m/v), corresponding to ≥18.5 to ≤70 mg of the toltrazuril or diclazuril in 1 ml.

In another embodiment the formulation used contains ≥10% (m/v) to ≤30% (m/v) of active iron.

The above values correspond to 100 to 300 mg active iron in 1 ml. Preferred are ≥11.4% (m/V) to ≤25% (m/V) corresponding to ≥114 mg to ≤250 mg active iron in 1 ml, especially preferably from ≥20% (m/V) to ≤25% (m/V), corresponding to ≥200 mg to ≤250 mg active iron in 1 ml of the formulation.

In another embodiment the formulation used contains ≥0.010% (m/v) to ≤10% (m/V) of the at least one surfactant with a HLB value of ≥10.

In another embodiment the polynuclear iron(III) polysaccharide complex compound is iron(III) dextran glucoheptonate or iron(III)dextrane, preferably iron(III) dextran glucoheptonate.

A specially preferred embodiment of the present invention, the formulation for use in the simultaneous treatment of coccidial infections and iron deficiencies in non-human animals consists of Toltrazuril iron(III) in the form of iron(III) dextran glucoheptonate, Phenole, at least one surfactant selected from the list consisting of Polysorbates and Sodium Docusat, simethicone emulsion, sodium chloride, water and optionally colloidal silicone dioxide and also optionally Polyvinylpyrrolidone.

Within said preferred embodiment, one particularly preferred formulation for use in the simultaneous treatment of coccidial infections and iron deficiencies in non-human animals consists of from 3 to 5 g/100 ml Toltrazuril, from 10 to 20 g/100 ml iron(III) in the form of iron(III) dextran glucoheptonate, from 0.3 to 0.8 g/100 ml Phenole, either from 0.05 to 0.2 g/100 ml Sodium Docusat or from 0.15 to 0.3 Polysorbates, wherein said Polysorbates are a mixture of from 0.1 to 0.2 g/100 ml Polysorbate 20 and from 0.05 to 0.1 g/100 ml Polysorbate 80, from 0.05 to 0.1 g/100 ml simethicone emulsion, from 0.8 to 1.1 g/100 ml sodium chloride, optionally about 0.5 g/100 ml colloidal silicone dioxide, optionally about 1 g/100 ml Polyvinylpyrrolidone and water.

Even more preferred is a formulation for use in the simultaneous treatment of coccidial infections and iron deficiencies in non-human animals consisting of about 5 g/100 ml Toltrazuril, from 15 to 20 g/100 ml iron(III) in the form of iron(III) dextran glucoheptonate, about 0.5 g/100 ml Phenole, from 0.1 to 0.2 g/100 ml Polysorbate 20 and from 0.05 to 0.1 g/100 ml Polysorbate 80, about 0.05 g/100 ml simethicone emulsion, about 0.9 g/100 ml sodium chloride and water, as well as a formulation for use in the simultaneous treatment of coccidial infections and iron deficiencies in non-human animals consisting of about 3 g/100 ml Toltrazuril, from 10 to 15 g/iron(III) in the form of iron(III) dextran glucoheptonate, from 0.6 to 0.7 g/100 ml Phenole, from 0.05 to 0.2 g/100 ml Sodium Docusat, about 0.1 g/100 ml simethicone emulsion, about 1 g/100 ml sodium chloride, about 0.5 g/100 ml colloidal silicone dioxide, about 1 g/100 ml Polyvinylpyrrolidone and water.

Within the just above referred to specially preferred embodiments, the non-human animal is preferably a piglet in the age of from birth to 96 h after birth, even more preferred a piglet either in the age from 24 h to 72 h or from 24 h to 96 h and the coccidiosis is caused by Cystoisospora suis.

In another embodiment the formulation used comprises a molar ratio of $Ca^{2+}$ to $Na^+$ from ≥0 to ≤3, more preferred from ≥0 to ≤1.

In another embodiment the formulation used has a total content of $CaCl_2$ and NaCl from ≥0.1% (m/V) to ≤5% (m/V). Preferred is ≥0.5% (m/v) to ≤4% (m/v), more preferred ≥0.9% (m/v) to ≤3% (m/v).

It has surprisingly been found that the presence of NaCl and $CaCl_2$ in the amounts specified in the two preceding embodiments increases the stability of the formulation over time.

In another embodiment the formulation has a content of free iron of ≤3500 ppm, preferably ≤2000 ppm and more preferred ≤1000 ppm.

Quantitative determination of dissolved iron ions may be achieved e.g. by dialysis of the sample with subsequent determination of dialyzed free iron with atomic absorption spectroscopy (AAS) or any other suitable method such as polarography and photometry.

In another embodiment the formulation, after storage at a temperature of ≥20° C. to ≤40° C. for 6 months, has a content of dissolved free iron ions of ≤3500 ppm, preferably ≤2000 ppm and more preferred ≤1000 ppm.

It is more preferred that the formulation has these contents after a storage of 12 months, even more preferred after 24 months and most preferred after 36 months. For example, the formulation, after storage at a temperature of ≥20° C. to ≤40° C. for 36 months, may have a content of free iron ions of ≤3500 ppm.

The measured content of iron ions mainly consists of two sources of iron ions. It's apparent that any iron ions that are already dissolved in the solvent of the formulation are part of the free iron according to the present invention.

A second source of free iron is any iron that is present in the as free iron in form of small complex fragments, known in literature as labile iron. In other words such free iron is no longer stably bound in the polysaccharide complex either intrinsically or by the fact that the polysaccharide complex compound has partially degraded or otherwise become defective.

Those complex fragments are transferred into $Fe^{2+}$ and/or $Fe^{3+}$ ions by suitable sample preparation methods and measured as described above together with the $Fe^{2+}$ and $Fe^{3+}$ ions which are originally present in the formulations.

Hence, it is understood in the scope of this invention, that the content of iron ions determined by AAS, polarography or photometry refers to the content of $Fe^{2+}$ and/or $Fe^{3+}$ ions freely dissolved in the formulation in addition to those transferred into freely dissolved ions upon sample preparation, while the $Fe^{2+}$ ions are not directly measured, as they are transferred to $Fe^{3+}$ anyway during sample preparation or by any other active means to result in measureable free iron in the form of freely dissolved $Fe^{3+}$ ions.

The term "free" iron in the scope of this invention and measured by the above mentioned methods thereby comprises all iron compounds which may cause toxicity after administration by overloading the iron transport capacity of the iron transport proteins mentioned earlier.

Consequentially, any amount of free iron measured by one of the methods described just above is always identical or bigger than the actual amount of "free" iron according to the functional definition given just above, as all measurement methods measure the overall amount of freely dissolved iron and non-functional complexes thereof, while only a portion thereof maybe actually harmful to the subject getting it administered.

The above described "free" iron needs to be separated from "active iron". For the purpose of the present invention, "active iron" is the amount of iron stably present in the polynuclear iron(III) polysaccharide complex compounds. From that alone and in the context of the present invention, active iron cannot be $Fe^{2+}$, but must be $Fe^{3+}$.

Furthermore, if—in the context of the present invention—weight percentages or ratios are disclosed with regard to said active iron, such amounts must always be considered to be stated without the respective amounts/weights of complex formation agents (i.e. the polysaccharide complex).

Therefore, in the context of the present invention, any reference made to a proportion of polynuclear iron(III) polysaccharide complex compound being part of any of the formulations used and disclosed herein, is to be understood as the amount of actual active iron(III) in said formulation that is thereafter made to become the polynuclear iron(III) polysaccharide complex compound by coordination with a polysaccharide complex. The actual amount of polynuclear iron(III) polysaccharide complex compound in any formulation used and disclosed is therefore significantly more than the actual "active iron".

The present invention will be further described with reference to the following examples without wishing to be limited by them.

EXAMPLES

Preparation of formulations used in examples 1 to 4.

Formulations of toltrazuril used in the following examples 1 to 4 are produced by weighing the necessary amount of toltrazuril into a beaker and dissolving it in about half of the amount of the lead solvent.

Next, if applicable, the specified amount of the co-solvent ethanol and the surfactants are added. The formulation is stirred until a clear solution is obtained. The formulation is transferred into a volumetric flask, tempered to 20° C. and filled with the lead solvent up the calibration mark (q.s to the desired volume). The formulations are sterile filtered into injection vials and closed with rubber stoppers and crimped caps.

List of Surfactants/Dispersants Used:

| (Trade) name(s) | Chemical classification or Pharm. Eur. Name |
| --- | --- |
| Kollidone ™ 17PF | Polyvinylpyrrolidone |
| Cremophor ™ EL/ Kolliphor ™ EL | Polyoxyl 35-hydrogenated castor oil (USP/NF) |
| Tween ™ 80 | Polysorbate 80 (Pharm. Eur.), Polyoxyethylen(20)-sorbitan-monooleat (IUPAC) |
| Pluronic ™ F68 | Poloxamer 188 (Pharm. Eur.), Ethylene Oxide/Propylene Oxide Block Copolymer, Poly(ethylene glycol)-block-poly(propylene glycol)-block-poly(ethylene glycol) |
| Lipoid ™ S100 | (purified) phosphatidylcholine from fatfree soybean lecithin |
| Vitamin E TPGS | Vitamine E-Tocopheryl-polyethyleneglycole-succinate |

Administration of the formulations used in examples 1 to 4 and evaluation: Aliquots of 1 ml/kg of the formulations were injected subcutaneously to female Wistar rats. Blood samples are collected at different time intervals and the plasma samples analyzed with regard to the concentration of toltrazuril in the plasma. From those data the AUC and Cmax values are determined according to standard methods, known to clinicians.

Example 1

Formulations of toltrazuril in the solvent dimethylsulfoxide (DMSO) are prepared according to Table 1 with the compositions of the formulations given in % mass per Volume (% M/V). The content of DMSO is meant as q.s. ad 100. In Table 2 the pharmacokinetic AUC and Cmax data and the change in compared to the reference formulation "ref" that does not comprise a surfactant are shown. [Note: "hr"=hours].

TABLE 1

| Formulations of Toltrazuril in DMSO | | | | | | | |
| --- | --- | --- | --- | --- | --- | --- | --- |
| Function | Ingredient | HLB | ref | 1 | 2 | 3 | 4 | 5 |
| API | Toltrazuril | n.a. | | | | | 1 | |
| Dispersant | Kollidone ™ 17PF | n.a. | — | — | — | — | — | 7.5 |
| Surfactant | Cremophor ™ EL | 12-14 | — | 10 | — | — | — | — |
| Surfactant | Tween ™ 80 | 15 | — | — | 10 | — | — | — |
| Surfactant | Vitamin E TPGS | 13.2 | — | — | — | 10 | — | — |
| Surfactant | Pluronic ™ F68 | 29 | — | — | — | — | 5 | — |
| Solvent | Ethanol | n.a. | | | | | 10 | |
| Solvent | DMSO | n.a. | 89 | 79 | 79 | 79 | 84 | 81.5 |

TABLE 2

| Pharmacokinetic data of formulations according to Example 1 | | | | | | |
| --- | --- | --- | --- | --- | --- | --- |
| PK data | Ref | 1 | 2 | 3 | 4 | 5 |
| AUC (hr*µg/L) | 778367 | 988485 | 1010307 | 922276 | 967051 | 810136 |
| % Change of AUC | — | +27 | +30 | +18 | +24 | +4 |
| Cmax (µg/L] | 11632 | 15920 | 14643 | 13887 | 13424 | 12638 |
| % Change of Cmax | — | +37 | +26 | +19 | +15 | +9 |

The above data clearly show the positive effect of the addition of surfactants with a HLB≥10, while the effect of the dispersant Kollidone™ 17PF which is not an amphiphilic compound and therefore intrinsically does not have a calculable HLB value, is considerably less.

Example 2

Formulations of toltrazuril in the solvent glycerol formal (4-Hydroxymethyl-1,3-dioxolan) are prepared according to Table 3 Table 1 with the compositions of the formulations given in % mass per Volume (% M/V). The content of glycerol formal is meant as q.s. ad 100. In Table 2 Table 4 the pharmacokinetic AUC and Cmax data and the change in % compared to the reference formulation "ref" that does not comprise a surfactant are shown. [Note: "hr"=hours]

TABLE 3

Formulations of Toltrazuril in glycerol formal

| Function | Ingredient | HLB | ref | 1 | 2 | 3 |
|---|---|---|---|---|---|---|
| API | Toltrazuril | n.a. | | 1 | | |
| Surfactant | Cremophor ™ EL | 12-14 | — | 10 | — | — |
| Surfactant | Tween ™ 80 | 15 | — | — | — | 10 |
| Surfactant | Vitamin E TPGS | 13.2 | — | — | 10 | — |
| Solvent | Glycerol formal (q.s. ad 100) | n.a. | 99 | 89 | 89 | 89 |

TABLE 4

Pharmacokinetic data of formulations according to Example 2

| PK data | ref | 1 | 2 | 3 |
|---|---|---|---|---|
| AUC (hr*µg/L) | 928370 | 1032468 | 969224 | 980867 |
| % Change of AUC | — | +11 | +4 | +6 |
| Cmax (µg/L] | 12785 | 14563 | 14825 | 16103 |
| % Change of Cmax | — | +14 | +16 | +26 |

The above data clearly show the positive effect of the addition of surfactants with a HLB≥10, which is less pronounced in the solvent glycerol formal, but still significant.

Example 3 (Comparative Example)

Formulations of toltrazuril in the solvent glycerol formal (4-Hydroxymethyl-1,3-dioxolan) and 10% ethanol are prepared according to Table 5 Table 1 with the compositions of the formulations given in % mass per Volume (% MN). The content of glycerol formal and 10% ethanol is meant as q.s. ad 100. In Table 6 Table 2 the pharmacokinetic AUC and Cmax data and the change in % compared to the reference formulation "ref" that does not comprise a surfactant are shown. [Note: "hr"=hours]

TABLE 5

Formulations of Toltrazuril in glycerol formal and 10% ethanol

| Function | Ingredient | HLB | ref | 1 |
|---|---|---|---|---|
| API | Toltrazuril | n.a. | 1 | |
| Surfactant | Lipoid ™ S100 | <10 | — | 10 |
| Solvent | Ethanol | n.a. | 10 | |
| Solvent | Glycerol formal (q.s. ad 100) | n.a. | 89 | 79 |

TABLE 6

Pharmacokinetic data of formulations according to Example 3

| PK data | ref | 1 |
|---|---|---|
| AUC (hr*µg/L) | 1012525 | 732434 |
| % Change of AUC | — | −28 |
| Cmax (µg/L] | 15452 | 12220 |
| % Change of Cmax | — | −21 |

The above data show that the addition of the surfactant Lipoid S100 which has a HLB of ≤10 results in a negative effect on the pharmacokinetic parameters.

Example 4

Formulations of toltrazuril in the solvent 2-pyrrolidone and 20 ethanol are prepared according to Table 7 Table 1 with the compositions of the formulations given in % mass per Volume (% M/V). The content of 2-pyrrolidone and 20 ethanol is meant as q.s. ad 100. In Table 8 the pharmacokinetic AUC and Cmax data and the change in 00 compared to the reference formulation "ref" that does not comprise a surfactant are shown. [Note: "hr"=hours]

TABLE 7

Formulations of Toltrazuril in 2-pyrrolidon and 20% ethanol

| Function | Ingredient | HLB | ref | 1 | 2 | 3 | 4 |
|---|---|---|---|---|---|---|---|
| API | Toltrazuril | n.a. | | 1 | | | |
| Surfactant | Tween ™ 80 | 15 | — | 10 | — | — | — |
| Surfactant | Cremophor ™ EL | 12-14 | — | — | 10 | — | — |
| Surfactant | Vitamin E TPGS | 13.2 | — | — | — | 10 | — |
| Surfactant | Pluronic ™F68 | 29 | — | — | — | — | 5 |
| Solvent | Ethanol | n.a. | | | 20 | | |
| Solvent | 2-Pyrrolidone | n.a. | 79 | 69 | 69 | 69 | 74 |

TABLE 8

Pharmacokinetic data of formulations according to Example 4

| PK data | ref | 1 | 2 | 3 | 4 |
|---|---|---|---|---|---|
| AUC (hr*µg/L) | 498930 | 676594 | 659221 | 515567 | 555691 |
| % Change of AUC | — | +36 | +32 | +3 | +11 |
| Cmax (µg/L) | 12396 | 16147 | 15545 | 13320 | 14473 |
| % Change of Cmax | — | +30 | +25 | +7 | +17 |

The above data clearly show the positive effect of the addition of surfactants with a HLB≥10 also in 2-pyrrolidone and 20% ethanol as a solvent.

Example 5

Examples 1 to 4 have shown the individual, positive effect of the addition of a surfactant of a HLB≥10. To show the combined effect of said surfactants with the addition of a polynuclear iron(III) polysaccharide complex, formulations as outlined in Table 9 were prepared in analogy to those disclosed in EP 2 164 496 A1.

TABLE 9

Formulations of Toltrazuril in water with and w/o Iron

| Function | Ingredient | HLB | Ref. | 1 |
|---|---|---|---|---|
| API | Toltrazuril | n.a. | 5 | 5 |
| API | Fe(III)Dextran | n.a. | — | 22.8 |
| Preservative | Sodium Proprionate | n.a. | 0.2 | |
| Preservative | Sodium Benzoate | n.a. | 0.2 | |
| Surfactant | Sodium Docusate | 10 | 0.25 | |
| Defoamer | Simethicone Emulsion USP 30% | n.a. | 0.05 | |
| Antifreezing | Propylene Glycol | n.a. | 10.5 | |
| pH-Regulator | Citric Acid | n.a. | 0.6-1.03 (ad pH ~4.5) | |
| Thickener | Bentonit/Xanthan gum | n.a. | 0.15-0.65 (ad ~150 mPa · s) | |
| Solvent | Water | n.a. | ad 100 | |

A total of 21 piglets born to 2 sows were randomly allocated to 2 study groups of 10 and 11 piglets each. Both formulations were administered in a single oral bolus to 3 day old piglets of the respective groups.

Frequent blood samplings (n=22 samples per piglet) were performed after treatment following a pre-determined schedule over a total period of 84 days, including a pre-treatment sample.

Concentrations of the active substance toltrazuril in plasma were analyzed by turbulent flow chromatography/tandem mass spectrometry. The limit of quantitation was 10 μg/L.

From the samples taken, the PK data of Table 10 were calculated.

TABLE 10

Pharmacokinetic data of formulations according to Example 5

| PK data | ref | 1 |
|---|---|---|
| AUC (day*mg/L) | 36.07 | 51.57 |
| % Change of AUC | — | +42.9 |
| Cmax (mg/L) | 8.44 | 10.07 |
| % Change of Cmax | — | +19.3 |

The above data clearly show the positive combined effect of the addition of a surfactant with a HLB≥10 with a polynuclear iron(III) polysaccharide complex compound.

While examples 1 to 4 showed the positive effect of the surfactant with a HLB≥10, the data generated as to Table 10 show an even further increased improvement of the relevant pharmacokinetic parameters.

Example 6

Examples 1 to 4 have shown the individual, positive effect of the addition of a surfactant of a HLB>10. Example 5 has shown the positive combined effect of said surfactants with the addition of a polynuclear iron(III) polysaccharide complex in an oral application.

To prove that the overall combined effect is not subject to a specific route of administration, formulations as outlined in Table 11 were prepared to be administered via injection. The "ref1" item is the same as outlined above in Example 5 to be the "ref" item, meaning an oral formulation only comprising toltrazuril. The "ref2" item is identical to the test item 1 of this example, but misses the addition of active iron.

Formulations were produced in analogy to Example 5.

TABLE 11

Formulations of Toltrazuril in water with and w/o Iron

| Function | Ingredient | HLB | Ref1. | Ref2. | 1 |
|---|---|---|---|---|---|
| API | Toltrazuril | n.a. | See | | 3 |
| API | Fe(III)Dextran-glucoheptonate | n.a. | Example | — | 18.2 |
| Preservative | Phenole | n.a. | 5 | | 0.5 |
| Surfactant | Tween ™ 20 | 16.7 | under | | 0.14 |
| Surfactant | Tween ™ 80 | 15 | "ref" | | 0.09 |
| Salt | Sodium Chloride | n.a. | | | 0.9 |
| Solvent | Water | n.a. | | | ad 100 |

In a parallel design 3 study groups of 6 piglets each were set-up. The animals were treated on their 3$^{rd}$ day of life with the respective items. The piglets of the group receiving the formulation as to ref1. received (just as above in Example 5) a single oral bolus, while the piglets of the respective two other groups received a single injection of the two formulations on their 3$^{rd}$ day of life. Frequent blood sampling was performed after each treatment at 0 h, 4 h, 8 h, 24 h, 32 h, 48 h, 72 h, 7 d, 14 d, 21 d and 28 d (n=11/animal). Concentrations of the active substance toltrazuril in plasma were analyzed by turbulent flow chromatography/tandem mass spectrometry. The limit of quantitation was 25 μg/L for each analyte.

From the samples taken, the PK data of Table 12 were calculated.

TABLE 12

Pharmacokinetic data of formulations according to Example 6

| PK data | Ref1 | Ref2 | 1 |
|---|---|---|---|
| AUC (hr*mg/L) | 897 | 1920 | 2224 |
| % Change of AUC | | +214 | +248 |

The above data clearly show the positive combined effect of the addition of a surfactant with a HLB≥10 with a polynuclear iron(III) polysaccharide complex compound regardless of route of administration, while the even higher HLB surfactants compared to that of Example 5 seems to further increase the positive effect on the pharmacokinetic properties achieved.

In summary of the above Examples 1 to 6 it can be established that surfactants of a HLB value of ≥10 substantially increase the already amended pharmacokinetic properties of a toltrazuril polynuclear iron(III) polysaccharide complex compound combination, that such effect is not bound to the formulation being a solution or dispersion of the actives and that such effect is neither subject of a specific route of application thereof

The invention claimed is:

1. A method for simultaneous treatment of coccidial infections and iron deficiencies in a non-human animal, the method comprising administering to the non-human animal a formulation comprising toltrazuril or diclazuril, a polynuclear iron(III) polysaccharide complex compound and at least two surfactants having a HLB value of 10 or more, wherein the at least two surfactants are Polysorbate 20 and Polysorbate 80.

2. The method according to claim 1, wherein the formulation is a suspension.

3. The method according to claim 1, wherein the formulation is orally administered.

4. The method according to claim 1, wherein the formulation is parenterally administered.

5. The method according to claim 4 wherein the formulation is administered by injection.

6. The method according to claim 1, wherein the formulation further comprises sodium chloride.

7. A method for simultaneous treatment of coccidial infections and iron deficiencies in a non-human animal, the method comprising administering to the non-human animal a formulation comprising toltrazuril, iron dextran glucoheptanoate, phenol, polysorbate 20, polysorbate 80, sodium chloride, and water.

* * * * *